United States Patent [19]
Ashman et al.

[11] Patent Number: 4,728,570
[45] Date of Patent: Mar. 1, 1988

[54] CALCIUM-HYDROXIDE-TREATED POLYMERIC IMPLANT MATRIAL

[75] Inventors: Arthur Ashman, New York, N.Y.; Itzhak Binderman, Tel Aviv, Israel

[73] Assignee: United States Surgical Corporation, Norwalk, Conn.

[21] Appl. No.: 792,352

[22] Filed: Oct. 29, 1985

[51] Int. Cl.$^4$ ............................................... A61K 6/08
[52] U.S. Cl. .................... 428/327; 428/330; 128/92 YG; 128/92 YQ; 623/16
[58] Field of Search .................. 623/16, 10; 428/323, 428/327, 330; 427/2; 128/92 YG, 92 YQ

[56] References Cited

U.S. PATENT DOCUMENTS

| | | | |
|---|---|---|---|
| 3,984,914 | 10/1976 | Schwartz | 623/16 X |
| 4,485,097 | 11/1984 | Bell | 623/16 X |
| 4,526,909 | 7/1985 | Urist | 623/16 X |
| 4,535,485 | 8/1985 | Ashman et al. | 623/10 X |
| 4,536,158 | 8/1985 | Bruins et al. | 433/201.1 |
| 4,536,523 | 8/1985 | Antonucci | 523/115 |

*Primary Examiner*—Nancy A. B. Swisher
*Attorney, Agent, or Firm*—Thomas R. Bremer

[57] ABSTRACT

An implant material for hard tissue comprising a porous matrix of a mass of biologically-compatible polymeric particles, the particles bonded together to form a unitary prosthetic implant, the prosthetic implant having interstices between the bonded particles forming pores into which bone tissue can grow and having a quantity of calcium hydroxide distributed in the pores of the matrix. Also disclosed is a packing material for forming in vivo prosthetic implants for hard tissue, the packing material comprising a mass of disjoint polymeric particles having an inner core and an outer coating and a quantity of calcium hydroxide distributed in the mass of polymeric particles effective to induce hard tissue growth.

23 Claims, No Drawings

CALCIUM-HYDROXIDE-TREATED POLYMERIC IMPLANT MATRIAL

TECHNICAL FIELD

The present invention concerns a porous implant material for inducing the growth of bone or other hard tissue into the pores of the implant material.

BACKGROUND ART

In the healing arts there is often a need for an implant material to replace, repair, or reconstruct hard tissue in the body of a patient. For example, hard-tissue implant materials are used in medicine and veterinary medicine as a prosthetic bone material to repair injured or diseased bone. Hard tissue implant materials are also used in the construction of prosthetic joints and to fix prosthetic joints to bone. In dentistry, hard tissue implant materials are used in the construction of prosthetic teeth and tooth roots and to replace or augment the edentulous ridge.

U.S. Pat. Nos. 4,535,485 (the '485 Pat. No.) and 4,536,158 (the '158 Pat. No.) disclose certain implantable porous prostheses for use as bone or other hard tissue replacement which are comprised of polymeric materials. The prostheses of the '485 and '158 Pat. Nos. are composed generally of polymeric particles. The particles have an inner core comprised of a first biologically-compatible polymeric material such as polymethylmethacrylate and an outer coating comprised of a second biologically-compatible polymeric material which is hydrophilic, such as polymeric hydroxyethylmethacrylate. The particles may incorporate a radioopaque material to render the particle visible in an X-ray radiograph. The particles may be bonded together to form a unitary structure which can be implanted in the body. Alternatively, a mass of the particles may be implanted in the body in an unbonded, granular form. In either the bonded or the unbonded form, interstices between the implanted particles form pores into which tissue can grow. The hydrophilic coating on the particles facilitates infusion of body fluids into the pores of the implant, which facilitates ingrowth of tissue into the pores of the implant.

Although porous prostheses of the '485 and '158 Pat. Nos. have proven to be satisfactory for many applications, there is room for improvement. For example, when it was attempted to graft together two bone fragments separated by a gap within the body of a rat by packing a mass of the polymeric particles in granular form in the gap, it was found that the tissue which grew into mass of particles was essentially cartilage and a dense fibrous connective tissue. Substantially no bone tissue formed in the gap packed with the particles between the two bone fragments. The joint between the two bone fragments was unacceptably fragile and nonrigid.

An article by Denissen and deGroot published in the *Journal of Prosthetic Dentistry*, volume 42, pages 551-556, (November, 1979) disclosed that implant materials based on calcium phosphate salts should be biocompatible and capable of forming tight bonds with surrounding bone. The article noted that previously available calcium-phosphate-based materials could be obtained only in a biodegradable form, which, although useful for bone replacement, was not useful for toothroot implants. Denissen and deGroot disclosed that a biostable tooth-root implant could be prepared by first preparing a porous implant form of biodegradable, sintered calcium hydroxylapatite and then coating and impregnating the implant form with polymeric poly (hydroxy-ethyl- methacrylate).

SUMMARY OF THE INVENTION

We have invented a porous implant material which can effectively induce the growth of hard tissue and which avoids problems of the prior art noted above.

Broadly, the implant material of the invention comprises a porous matrix which is comprised of a biologically- compatible polymeric mateial. The pores of the matrix have dimensions effective to permit the growth of hard tissue into the pores.

The implant material of the invention further comprises a quantity of calcium hydroxide distributed in the pores of the matrix. The quantity of calcium hydroxide is effective to induce the growth of hard tissue in the pores.

Preferably, the porous matrix comprises a mass of polymeric particles bonded together to form a unitary prosthetic implant. Each polymeric particle has an inner core comprised of a first biologically-compatible polymeric material and an outer coating comprised of a second biologically-compatible polymeric material which generally surrounds the inner core. The second polymeric material is hydrophilic and has a composition which is different from the composition of the first polymeric material. Pores into which hard tissue can grow are formed by interstices between the bonded particles.

For the preferred implant material of the invention comprised of a mass of coated particles bonded together, the first polymeric material of which the cores of the particles are comprised is preferably an acrylic polymer. Most preferably, the first polymeric material is polymethylmethacrylate (PMMA). The second polymeric material is preferably a polymeric hydroxyethylmethacrylate (PHEMA). Most preferably, the polymeric hydroxyethylmethacrylate comprises a copolymer of monomeric hydroxyethylmethacrylate and a cross-linking agent. Preferred cross-linking agents include triethyleneglycol dimethacrylate, tetraethyleneglycol dimethacrylate, diethyleneglycol dimethacrylate, and monoethyleneglycol dimethacrylate. The cross-linking agents preferably comprise from about 0.1 percent to about 5 percent by weight of the monomeric hydroxyethylmethacrylate.

A preferred porous matrix comprised of a mass of coated particles is disclosed in U.S. Pat. No. 4,536,158, the specification of which is hereby incorporated by reference.

For many applications, it is preferred for the implant material of the invention to be in a granular form. Such a granular implant material can constitute a packing material for forming prosthetic implants for hard tissue in vivo. A preferred granular implant material comprises a mass of disjoint polymeric particles. Each particle has an inner core comprised of a first biologically-compatible polymeric material and has an outer coating comprised of a second biologically-compatible polymeric material which generally surrounds the inner core. The second polymeric material is hydrophilic and has a composition different from the compositon of the first polymeric material. The polymeric particles are of a size to permit the mass of the disjoint particles to be packed in a body cavity to form a prosthetic implant for hard tissue with interstices between compacted particles of the prosthetic implant forming pores into which tissue can grow. The granular implant material of the invention further comprises a predetermined quantity of calcium hydroxide distributed in the mass of polymeric particles. The quantity of calcium hydroxide is effective to induce the growth of hard tissue in the pores of the mass of particles when packed in a body cavity. Preferably, the calcium hydroxide forms a coating on outer surfaces of the polymeric particles.

Preferably, the polymeric beads of the granular implant material include a non-bonding agent such as barium sulfate to prevent the particles from bonding together. The calcium hydroxide is expected to assist in preventing the polymeric particles from bonding together. The first polymeric material is most preferably PMMA, although other acrylic polymers are also preferred. The PMMA may include a plasticizer, if desired. The second polymeric material is most preferably PHEMA. Preferred polymeric beads for preferred granular implant materials of the invention are disclosed in U.S. Pat. No. 4,535,485, the specification of which is hereby incorporated by reference.

Preferred procedures for producing a porous matrix for implant materials of the invention are set forth in the specification of the '158 Pat. No. incorporated herein by reference. Preferably, calcium hydroxide is introduced into the pores of the porous matrix by soaking the matrix in an aqueous solution of calcium hydroxide, then removing any excess solution from the matrix and allowing the matrix to dry. Preferred aqueous solutions of calcium hydroxide have a concentration in the range of from about 0.05 percent to about 1.0 percent calcium hydroxide by weight.

Preferred procedures for producing polymeric particles for granular implant materials of the invention are set forth in the specification of the '485 Pat. No. incorporated herein by reference. Preferably, calcium hydroxide is deposited on outer surfaces of the polymeric particles by soaking the particles in an aqueous solution of calcium hydroxide, separating the particles from the solution by filtering, and then drying the particles. Preferred aqueous soutions of calcium hydroxide have a concentraton in the range of from about 0.05 percent to about 1.0 percent calcium hydroxide by weight.

It is ordinarily preferred to include a radio-opaque compound such as barium sulfate in the implant material of the invention to render the implant visible on an X-ray radiograph.

Preferred hard-tissue implant materials of the invention are inexpensive to manufacture and may be used to advantage in many medical, dental and veterinary applications. Preferred implant materials of the invention which are rigid can be formed into a variety of shapes to form prosthetic implants. For example, preferred implant materials of the invention can be shaped to form prosthetic sections of bone, including sections of the jawbone. Prosthetic tooth roots can also be formed from such materials. Preferred granular implant materials can readily be packed in irregularly-shaped bony cavities of the body to fill and conform to the shape of the cavity. In general, it is expected that preferred implant materials of the invention can be used to advantage in applications disclosed for polymeric implant materials in the '158 and '485 Pat. Nos. cited above.

Preferred implant materials of the invention are remarkably effective in inducing bone growth. Such implant materials can be used to graft fragments of bone together which are separated by a gap of several millimeters or more. Advantageously, packing such a gap with a preferred granular implant material of the invention can in many circumstances induce new bone tissue to grow in the gap through the implant material to form a strong bond between the bone fragments. It is anticipated, therefore, that preferred implant materials of the invention will find wide use in treating bone fractures and in orthopedic surgery.

EXAMPLES

A series of experiments were run to compare the implant material of the invention with conventional bone implant materials with regard to uniting relatively wide gaps in the long bones of rats.

Six implant materials were obtained as described below.

A super-saturated solution of calcium hydroxide was prepared by dissolving about 0.5 g of $Ca(OH)_2$ in about 100 ml of distilled water. The resulting solution was filtered through an approximately 0.45$\mu$m filter in a sterile filtration unit. The filtered calcium hydroxide solution had a pH in the range of from about 12 to about 13.

(1) Untreated PHEMA-coated PMMA beads.

Approximately 10 g of PHEMA-coated PMMA beads were obtained. The beads were sterile and approximately 20-24 mesh in size. The PHEMA-coated PMMA beads incorporated roughly ten percent barium sulfate by volume relative to the volume of the uncoated PMMA beads. The PHEMA-coated PMMA beads, commercially available from Medical Biological Sciences, Inc. of New York, N.Y. under the trade name "HTR," were prepared according to the procedure disclosed in U.S. Pat. No. 4,535,485.

(2) PHEMA-coated PMMA beads treated with $Ca(OH)_2$

Approximately 10 g of the PHEMA-coated PMMA beads described in subsection (1) was mixed with approximately 2 ml of the approximatey 0.5 pecent by weight calcium hydroxide solution described above. The beads were allowed to soak in the solution at room temperature for about 15-20 minutes. The beads were then separated from the solution by filtering and dried in a thin layer under a vacuum.

(3) Untreated Kiel bone

Approximately 10 g of an implant material known as "Kiel bone" was obtained. Kiel bone is a particulate material which consists of partly deproteinised bone prepared from freshly killed calves. Kiel Bone is commercially available from Braun Milsungen A. G. of Milsungen, West Germany. The Kiel bone was ground to particles of a size in the range of from about 70 to about 400$\mu$m.

(4) Kiel bone treated with $Ca(OH)_2$

Approximately 10 g of Kiel bone as described in subsection (3) above was ground to particles of the size of from about 70 to about 400 $\mu$m. The particles of Kiel bone were then mixed with approximately 2 ml of the calcium hydroxide solution described above and allowed to soak at room temperature for about 15-20 minutes. The particles of Kiel bone were then separated from the solution by filtering and dried in a thin layer under a vacuum.

(5) Kiel bone treated with neutralized $Ca(OH)_2$

Approximately 10 ml of the calcium hydroxide solution described above was titrated with approximately 0.1 N orthophosphoric acid to a pH of about 7.4. The procedure of subsection (4) above was then repeated using the calcium hydroxide solution thus titrated for the untitrated calcium hydroxide solution of subsection (4).

(6) Kiel Bone and Bone Marrow

Bone marrow was accumulated from the femori of rats of the same strain as those on which the bone grafts were made. Approximately 10 g of Kiel bone ground to a particle size of from about 40 to about 700 μm was combined with about 30 percent by volume of the bone marrow.

Forty-two young albino rats each weighing from about 120 to about 150 g were divided into seven groups of six rats. In each of the rats, the right femur was exposed. With a low-speed dental drill using a corborundum disc, an ostectomy was performed in the midshaft of the femur to divide the bone into two fragments with a gap of from about 3 to about 4 mm in width between them. A length of stainless steel wire was shaped to an "omega" form and its free ends were inserted into the shafts of the two ends of the bone fragments. The wire served to fix the fracture. In addition, the wire maintained the gap between the two ends of the bone fragments and thus created a model for a non-union.

For six of the groups of rats, after the wire was inserted the gap was immediately filled with roughly 250 mg of one of six bone-grafting materials identified above. One group of six rats received no implant material and served as a control group. The muscles were then reflected and the skin was sutured with 3-0 chromic cat-gut sutures.

The rats were sacrificed 36 days after the implantation and the femurs which had been severed were prepared for histological examination. The sections were evaluated microscopically for the development of fibrous connective tissue, cartilage and trabecular bone. The results of the examination are summarized in Table I below.

Examination of the control animals showed that when the two fragments of the femur were kept apart by the aid of a looped wire, a fibrous type of tissue tended to develop in the gap between the fragments, producing a non-union bone healing. From Table I, group 0, it may be seen that during 36 days after implantation, bone bridging did not occur in any of the animals in the control group. In all rats of the control group, substantially only loose fibrous tissue developed in the gap between the two bone fragments, although in certain of the control animals locci of cartilage were observed.

When untreated PHEMA-coated PMMA beads filled the gap, dense connective tissue tended to grow in response (Table I, group 1). The PHEMA-coated PMMA bead material induced a very mild cellular response with almost no macrophage type cells in their neighborhood.

PHEMA-coated PMMA beads treated with calcium hydroxide produced a graft which tended to induce bone formation in the gap (Table I, group 2). The new bone tissue thus formed produced a solid support. Cartilage and bone cells grew very close to the calcium-hydroxide treated PHEMA-coated PMMA beads, with substantially no intermediate layers of fibroblasts.

When particles of untreated Kiel bone filled the gap, fibrous tissue tended to surround the particles (Table I, group 3). The fibrous tissue was more dense than the fibrous tissue which developed in the gap between the bone fragments in the control animals. Many macrophages and less multinucleated cells which were osteoclast-like were seen in the near vicinity of the Kiel bone. Some new bone appears to have been formed at the bone fragments.

The Kiel bone which was treated with calcium hydroxide prior to implantation stimulated the formation of a rigid callus with components of cartilage and bone (Table I, group 4). This group showed a long rigid bridge between the bone fragments which filled the gap. Some spaces were still filled with dense connective tissue, which we anticipate would remodel into bone with time.

When the Kiel bone was treated with calcium hydroxide which had been substantially neutralized with orthophosphoric acid, the bone induction ability of the material was significantly inhibited (Table I, group 5).

Kiel bone mixed with autogenous bone marrow developed into cartilage and bone bridging the bone gap (Table I, group 6).

Of all the Kiel bone implant materials, the most solid and mature bone bridge was formed by Kiel bone mixed with marrow, followed by Kiel bone treated with calcium hydroxide. In comparison to Kiel bone treated with calcium hydroxide, the PHEMA-coated PMMA beads treated with calcium hydroxide appeared to be superior, since no fibroblast cellular interphase was seen between bone or cartilage. While the Kiel bone treated with calcium hydroxide induced much giant cell and macrophage response, the PHEMA-coated PMMA beads treated with calcium hydroxide did not induce any adverse cellular response.

It is not intended to limit the present invention to the specific embodiments described above. It is recognized that changes may be made in the implant materials specifically described herein without departing from the scope and teaching of the instant invention, and it is intended to encompass all other embodiments, alternatives and modifications consistent with the invention.

TABLE I

| Group | Fibrous Tissue | Cartilage | Trabecular Bone |
| --- | --- | --- | --- |
| 0. Control | L++ | ++ | — |
| 1. PHEMA-coated PMMA | D+++ | + | — |
| 2. PHEMA-coated PMMA + Ca(OH)$_2$ | — | ++ | +++ |
| 3. KB | D+++ | + | — |
| 4. KB + Ca(OH)$_2$ | D+ | +++ | + |
| 5. KB + Ca(OH)$_2$ neutralized with H$_3$PO$_4$ | D++ | ++ | — |
| 6. KB + Marrow | — | +++ | ++ |

L - Loose Connective Tissue
D - Dense Connective Tissue
KB - Kiel bone

We claim:

1. An implant material for hard tissue, the implant material comprising a porous matrix comprised of a mass of biologically-compatible polymeric particles, the particles being bonded together to form a unitary prosthetic implant, the prosthetic implant having interstices between the bonded particles forming pores into which bone tissue can grow and a quantity of calcium hydroxide distributed in the pores of the matrix, the pores having dimensions effective to permit the growth of bone tissue into the pores, the quantity of calcium hydroxide being effective to induce the growth of bone tissue in the pores.

2. The implant material according to claim 1 in which each of said biologically-compatible polymeric particles has an inner core comprised of a first biologically-compatible polymeric material and has an outer coating generally surrounding the inner core, the outer coating being comprised of a second biologically-compatible polymeric material, the second material being hydrophilic and having a composition different from the composition of the first polymeric material.

3. The implant material according to claim 2 in which the first polymeric material is an acrylic polymer.

4. The implant material according to claim 3 in which the first polymeric material is polymethylmethacrylate.

5. The implant material according to claim 3 in which the second polymeric material is a polymeric hydroxyethylmethacrylate.

6. The implant material according to claim 5 in which the polymeric hydroxyethylmethacrylate comprises a copolymer of monomeric hydroxyethylmethacrylate and a cross-linking agent.

7. The implant material according to claim 5 in which the prosthetic implant is shaped to form a tooth root.

8. The implant material according to claim 5 in which the prosthetic implant is shaped to form section of bone.

9. The implant material according to claim 8 in which the prosthetic implant is shaped to form a section of jawbone.

10. The implant material according to claim 1 further including a radiopaque material.

11. The implant material according to claim 10 in which the radiopaque material is barium sulfate.

12. The implant material according to claim 1 in which the pores have a size of from about 350 to about 415μm.

13. A packing material for forming in vivo prosthetic implants for hard tissue, the packing material comprising:
(a) a mass of disjoint polymeric particles, each particle having an inner core comprised of a first biologically-compatible polymeric material and having an outer coating generally surrounding the inner core, the outer coating being comprised of a second biologically-compatible polymeric material, the second polymeric material being hydrophilic and having a composition different from the composition of the first polymeric material, the particles being of a size to permit the mass of the disjoint particles to be packed in a body cavity to form a prosthetic implant for hard tissue with interstices between compacted particles of the prosthetic implant forming pores into which tissue can grow; and
(b) a quantity of calcium hydroxide distributed in the mass of polymeric particles, the quantity of calcium hydroxide being effective to induce the growth of hard tissue in the pores of the mass of the particles when packed in a body cavity.

14. The packing material of claim 13 in which the diameter of the polymeric particles is in the range of from about 590 to about 840 μm.

15. The packing material of claim 14 in which the first polymeric material is an acrylic polymer.

16. The packing material of claim 15 in which the first polymeric material is polymethylmethacrylate.

17. The packing material of claim 15 in which the second polymeric material is a polymeric hydroxyethylmethacrylate.

18. The packing material according to claim 13 in which the calcium hydroxide forms a coating on outer surfaces of the polymeric particles.

19. The packing material according to claim 18 in which the coating of calcium hydroxide on the polymeric particles is formed by wetting the mass of polymeric particles with an aqueous solution of calcium hydroxide and then allowing the solution to dry.

20. The packing material according to claim 19 in which the concentration of calcium hydroxide in the calcium hydroxide solution is in the range of from about 0.05 to about 1 percent by weight.

21. A packing material for forming in vivo prosthetic implants for hard tissue, the packing material comprising:
(a) a mass of disjoint biologically-compatible polymeric particles, the particles being of a size to permit the mass of the disjoint particles to be packed in a body cavity to form a prosthetic implant for hard tissue with interstices between compacted particles of the prosthetic implant forming pores into which tissue can grow; and
(b) a quantity of calcium hydroxide coated on the outer surfaces of said biologically-compatible polymeric particles, the quantity of calcium hydroxide being effective to induce the growth of hard tissue in the pores of the mass of the particles when packed in a body cavity.

22. The packing material according to claim 21 wherein the biologically-compatible polymeric particles are comprised of an acrylic polymer.

23. The packing material according to claim 22 wherein the acrylic polymer is polymethylmethacrylate.

* * * * *